United States Patent
Soennichsen et al.

(10) Patent No.: US 8,231,904 B2
(45) Date of Patent: Jul. 31, 2012

(54) EXTENDED RELEASE FORMULATION FOR PRALNACASAN

(75) Inventors: Caren Soennichsen, Frankfurt am Main (DE); Roland Wesch, Frankfurt am Main (DE); Heiko Meier, Biberach (DE)

(73) Assignee: Sanofi-Aventis Deutschland GmbH, Frankfurt am Main (DE)

( * ) Notice: Subject to any disclaimer, the term of this patent is extended or adjusted under 35 U.S.C. 154(b) by 0 days.

(21) Appl. No.: 12/062,683

(22) Filed: Apr. 4, 2008

(65) Prior Publication Data

US 2008/0279934 A1     Nov. 13, 2008

Related U.S. Application Data

(63) Continuation of application No. PCT/EP2006/009466, filed on Sep. 29, 2006.

(30) Foreign Application Priority Data

Oct. 8, 2005  (DE) .......................... 10 2005 048 293

(51) Int. Cl.
*A61K 9/22*     (2006.01)
*A61K 31/47*    (2006.01)

(52) U.S. Cl. ........................................ 424/468; 514/307

(58) Field of Classification Search .................. None
See application file for complete search history.

(56) References Cited

U.S. PATENT DOCUMENTS

| 5,085,865 A | 2/1992 | Nayak |
| 5,681,583 A | 10/1997 | Conte et al. |
| 2004/0170680 A1 * | 9/2004 | Oshlack et al. ............... 424/457 |
| 2005/0013863 A1 | 1/2005 | Lim et al. |
| 2005/0053653 A1 | 3/2005 | Kidane et al. |

FOREIGN PATENT DOCUMENTS

| WO | WO 2005/048979 | * | 6/2005 |
| WO | WO 2005/051350 | * | 6/2005 |

* cited by examiner

*Primary Examiner* — David J Blanchard
*Assistant Examiner* — Tigabu Kassa
(74) *Attorney, Agent, or Firm* — Ronald G. Ort; Scully, Scott, Murphy & Presser, P.C.

(57) ABSTRACT

This invention relates to a sustained release tablet comprising at least two layers, wherein at least one layer rapidly releases pralnacasan and the other layer releases pralnacasan in a delayed manner. This tablet is particularly suitable for the treatment of a condition such as autoimmune diseases, type I and type II diabetes, rheumatoid arthritis, osteoarthritis or psoriasis.

3 Claims, 2 Drawing Sheets

EXTENDED RELEASE FORMULATION FOR PRALNACASAN

CROSS REFERENCE TO RELATED APPLICATIONS

This application is a continuation of PCT/EP2006/009466 filed on Sep. 29, 2006, which claims benefit of priority of German Application No. 102005048293.7 filed on Oct. 8, 2005, the entire contents of each of which are incorporated herein by reference.

The invention relates to an extended release formulation comprising pralnacasan.

Pralnacasan (1S,9S(RS,3S)N-(2-ethoxy-5-oxo-tetrafuran-3-yl)-6,10-dioxo-9-(isoquinolin-1-oylamino)-1,2,3, 4,7,8,9, 10-octahydro-6-H-pyridazino[1,2-a][1,2]-diazepine-1-carboxamide and its salts and derivatives are disclosed in WO 97/22619 for the treatment for example of autoimmune diseases, rheumatoid arthritis, osteoarthritis, type I and type II diabetes and psoriasis. The compound which is effective in this regard is the open-chain compound 3S(1S,9S)3-[6,10-dioxo-9(isoquinolin-1-oylamino)-1,2,3,4,7,8,9,10-octahydro-6H-pyridazino[1,2-a][1,2]-diazepine-1-carboxamido]-4-oxobutanoic acid, while pralnacasan is the prodrug or pharmaceutical agent thereof. WO 97/22619 also describes a standard table for rapid release of the prodrug.

It was an object of the invention to provide an extended release tablet which makes it possible with only twice daily dosage to make it possible for the delivery of pralnacasan and/or its salts and/or derivatives to be uniform with, at the same time, a reduced total daily dose compared with the standard tablet.

The object is achieved by an extended release tablet comprising at least two layers, where at least one layer delivers the pralnacasan and/or its salts and/or its derivatives rapidly (initial dose) and at least a second layer which delivers pralnacasan and/or its salts and/or derivatives in an extended fashion (maintenance dose). The layers may be stacked in sandwich fashion but may also be disposed as core and shell.

Figure 1:
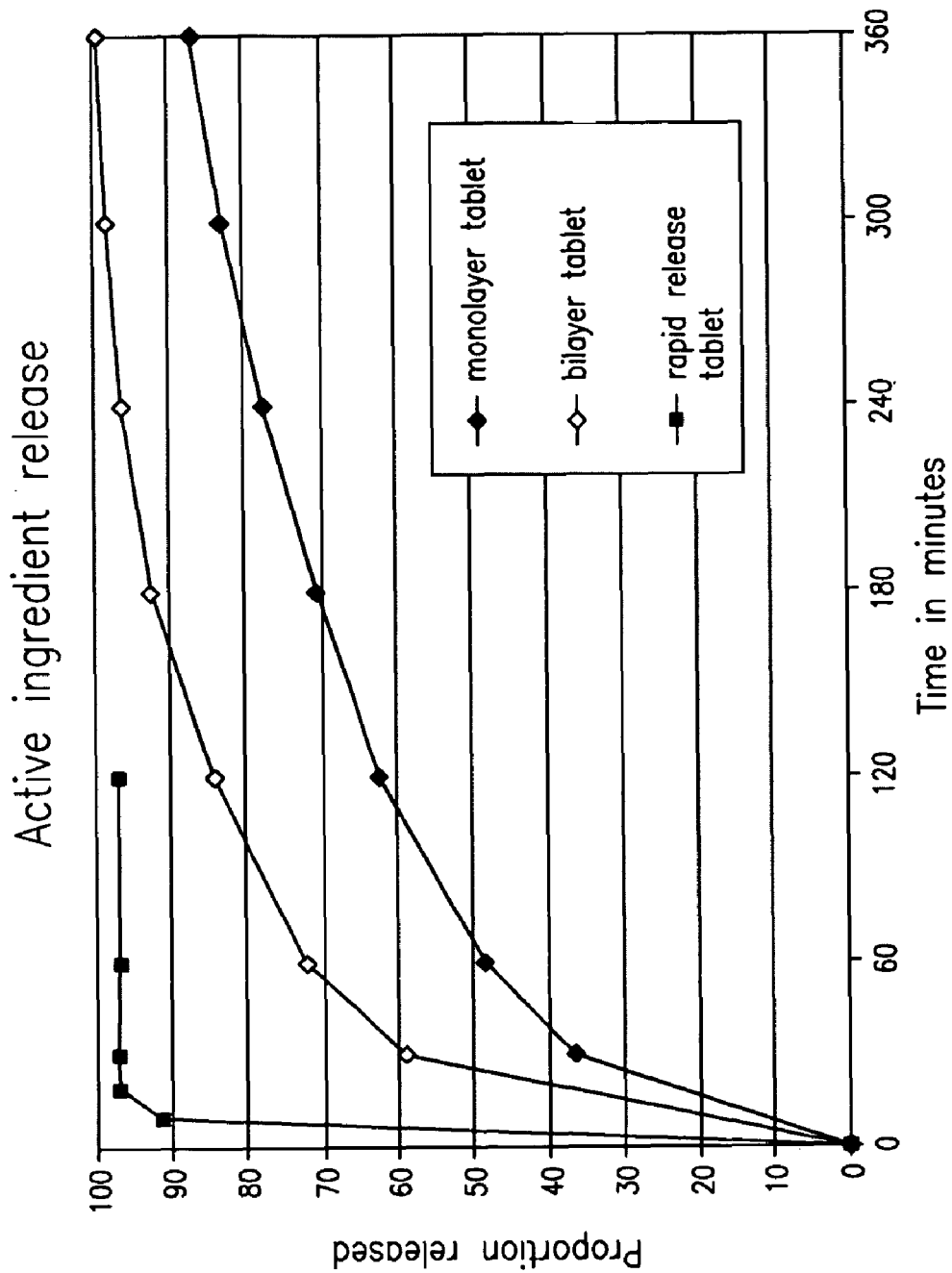
FIG. 1 is a graph comparing the active ingredient release of the formulation of the present invention with a rapid release tablet and with an extended release tablet.

"Rapid" delivery means that at least 60% of pralnacasan or its salts and/or derivatives is released from the tablet within only 30 minutes. "Extended" delivery means that at least 90% of pralnacasan or its salts and/or derivatives are released after 180 minutes. In this case, the absorption window is prolonged from 6 h to 8 h.

In conventional tablets which deliver the pharmaceutical agent rapidly, pralnacasan has insufficient efficacy or would need to be used in such a high dose that unwanted side effects are to be feared. Administration three times a day, which would avoid a single high dosage, is not however desirable in terms of patient compliance. On the other hand, a conventional extended release tablet is likewise unsatisfactory for administration twice a day (release of pharmaceutical agent over 2×6=12 h) because, firstly, the release of pharmaceutical agent takes place too slowly, so that sufficiently high, therapeutically effective blood levels are not reached initially, and, secondly, the proportion of pharmaceutical agent which is not released until the lower segment of the intestine (large intestine) is not absorbed there and thus remains ineffective. A combination of conventional tablet with extended release tablet also appeared undesirable, however, because the two parts of such a tablet normally have adverse effects on one another.

It is surprisingly found with the extended release tablet having at least two layers according to the invention that rapid delivery of the pharmaceutical agent is not adversely affected by the extended release part, i.e. the layer(s) with the initial portion made it possible for the onset of action of the extended release tablet of the invention surprisingly to be no slower than that of the standard tablet, and the extended release portion is absorbed sufficiently long and completely, although this portion is absorbed exclusively in the upper GT tract, i.e. the extended release portion is not only not adversely affected by the initial portion but, surprisingly, is in fact beneficially affected. This mode of action in particular was not predictable for a combination tablet.

With the extended release tablet of the invention there is surprisingly prevention of large blood level peaks which are normally responsible for toxic side effects of a pharmaceutical agent. Patient compliance is improved through use of the extended release tablet of the invention, because less pharmaceutical agent needs to be taken per day in larger doses. Despite a plurality of layers of the pharmaceutical agent, the required extended release tablet is not more voluminous than a standard tablet. This is important and advantageous in particular for elderly patients.

The extended release tablet of the invention preferably consists of two layers which are disposed both as core and shell, preferably concentrically as spheroid or as ellipsoid, and as stacked layers. The layered tablet may be a tablet having a circular or oval outline. In the core-shell arrangement, the initial dose is preferably located in the outer shell, and the extended release dose is located in the core region.

The preferably two layers of the tablet of the invention may in each case comprise besides the pharmaceutical agent in each case one or more fillers, preferably two or three, and one or more binders, one binder is preferred, and one or more, preferably one, lubricant. The fillers, binders and lubricants may be different in the respective layers of each tablet. The number thereof may also differ in each case. It is preferred for three different fillers to be present in the extended release layer, whereas there are two different fillers in the rapid release layer.

The binders and lubricants present in the layers are preferably the same.

The extended release layer additionally further comprises one or more gel formers, especially when the extended release layer represents the outer layer of the tablet. One gel former is preferred.

The rapid release layer additionally comprises one or more disintegrants, one disintegrant is preferred.

Examples of fillers are corn starch, phosphates such as calcium phosphate, lactose, e.g. lactose D80, sucrose, such as mannitol or microcrystalline celluloses, e.g. type 102. Lactose, mannitol or microcrystalline cellulose are preferred. The fillers are present in the respective layers in the range 0-400 mg/layer, preferably 10-200, particularly preferably 20-100. If two or three fillers are to be present per layer, these are present in the ratio of about 2:1 or 2:1:1. If two fillers are to be present, they are preferably lactose D80 and mannitol or microcrystalline cellulose.

If three fillers are to be present, they are preferably lactose D80, microcrystalline cellulose and mannitol.

The extended release layer preferably comprises three fillers, and the rapid release layer two fillers.

Suitable binders are in general cellulose ethers or polyvinylpyrrolidone. Hydroxypropylcellulose in the range 5-30 mg/layer is preferred, preferably 10-20 mg/layer.

Lubricants may be the stearates known to the skilled worker, such as magnesium stearate and fumarates, e.g. sodium stearyl fumarate. 5-20 mg thereof are present in each layer, and 1-5 mg of lubricant are preferably present in the rapid release layer.

The extended release layer additionally comprises one or more gel formers such as, for example, hydroxypropylmethylcellulose or carrageenan, preferably hydroxypropylmethylcellulose in the range 20-100 mg/layer, particularly preferably 30-50 mg/layer. The rapid release layer additionally comprises at least one disintegrant such as, for example, croscarmellose or crospovidone, preferably croscarmellose, in the range 5-20 mg/layer, preferably 6-15 mg/layer.

All the ingredients of the tablet which occur in the two layers are in principle present in the ratio 1.5-1.0 to 3.0-1.0, preferably 2.0-1.0 in the extended release layer compared with the rapid release layer.

This also applies to as pharmaceutical agent. The extended release layer comprises 200-600 mg of pharmaceutical agent/layer, preferably 300-500 mg/layer. The rapid release layer comprises 50-400 mg of pharmaceutical agent/layer, preferably 100-300 mg/layer.

The ratio is preferably 400:200 mg/layer. Suitable as pharmaceutical agent is pralnacasan and/or its derivatives and the respective salts, as well as the respective active compounds (free acids).

It is also possible for mixtures of pralnacasan and/or its salts and/or its derivatives or mixtures of the respective free acids to be present. Mixtures of pralnacasan or its derivatives with the free acids can also be employed.

The extended release tablet of the invention is manufactured by granulating the pharmaceutical agent. These granules are mixed with the additional excipients such as filler, binder and lubricant. Finally, specifically for the extended release layer, the gel former is added, and the disintegrant is added to the rapid release layer. The two layers are compressed together to give a tablet.

FIG. 1 compares the active ingredient release of the extended release formulation of the invention (bilayer tablet) with a rapid release tablet and an extended release tablet (monolayer tablet).

Figure 2:
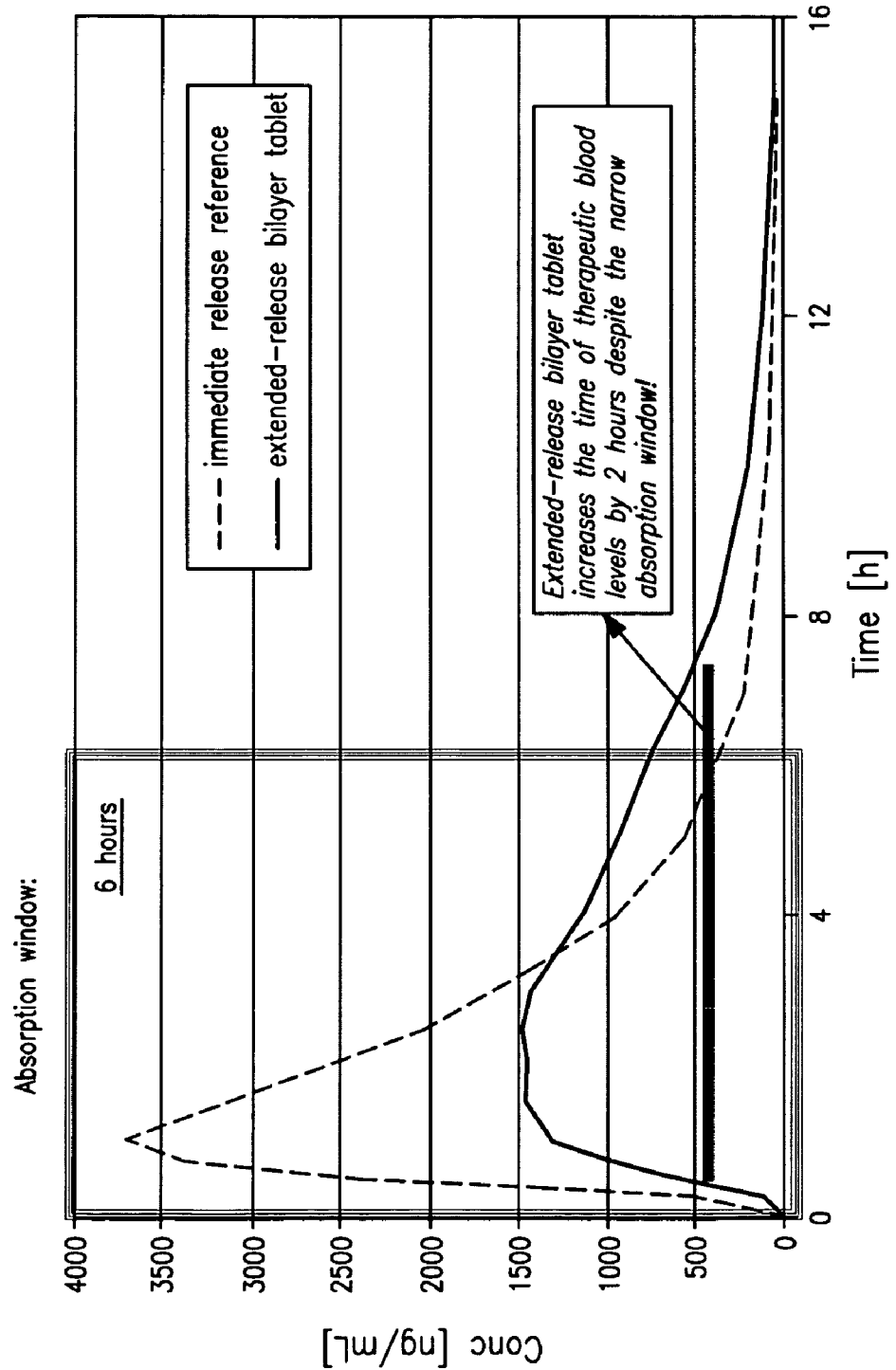
FIG. 2 is a graph comparing the blood level concentration over time of the formulation of the present invention with a rapid release tablet and with an extended release tablet.

It surprisingly emerges that until the tablet of the invention at least 60% of the pharmaceutical agent is released after only 30 minutes, and at least 90% after 180 minutes. As shown in FIG. 2, the tablet of the invention thus prolongs the therapeutic concentration in the blood by 2 hours beyond the narrow absorption window of 6 hours compared with the rapid release tablet.

The extended release formulation of the invention is preferably for the treatment of autoimmune diseases, type I and type II diabetes, rheumatoid arthritis, osteoarthritis and psoriasis. In general, all the disorders mentioned in WO 97/22619 can be treated with the extended release tablets of the invention.

The extended release formulation of the invention can be administered orally in the form of capsules and tablets. The extended release formulation as preferably administered once a day. The dose of the pharmaceutical agent is from 0.01 to 100 mg/kg of body weight per day, preferably 1 to 50 mg/kg of body weight per day.

The invention is to be made clear by the following examples (bilayer tablet):

|  | Extended release layer |
|---|---|
| Pralnacasan | 400 |
| Lactose D 80 | 62 |
| Hydroxypropylcellulose | 18 |
| Microcrystalline cellulose type 102 | 30 |
| Hydroxypropylmethylcellulose 4000 mPas | 40 |
| Mannitol | 30 |
| Magnesium stearate | 10 |
| TOTAL | 590 |

|  | Rapid release layer |
|---|---|
| Pralnacasan | 200 |
| Lactose D 80 | 31 |
| Croscarmellose | 10 |
| Hydroxypropylcellulose | 9 |
| Microcrystalline cellulose type 102 | 15 |
| Magnesium stearate | 1.5 |
| TOTAL | 266.5 |

|  | Complete tablet |
|---|---|
| HMR 3480 | 600 |
| Lactose D 80 | 93 |
| Hydroxypropylcellulose | 27 |
| Croscarmellose | 10 |
| Microcrystalline cellulose type 102 | 45 |
| Hydroxypropylmethylcellulose 4000 mPas | 40 |
| Mannitol | 30 |
| Magnesium stearate | 11.5 |
| TOTAL | 856.5 |

Data in mg/tablet

What is claimed is:

1. A two-layer extended release tablet for the oral administration of pralnacasan, or a salt thereof, comprising a rapid release layer comprising pralnacasan and croscarmellose as a disintegrant, and an extended release layer comprising pralnacasan and hydroxypropylmethylcellulose as a gel former, wherein both layers comprise at least one filler, at least one binder and at least one lubricant; wherein the rapid release layer consists essentially of: 200 mg pralnacasan, 31 mg lactose D 80, 10 mg croscarmellose, 9 mg hydroxypropylcellulose, 15 mg microcrystalline cellulose type 102, and 1.5 mg magnesium stearate; and the extended release layer consists essentially of: 400 mg pralnacasan, 62 mg lactose D 80, 18 mg hydroxypropylcellulose, 30 mg microcrystalline cellulose type 102, 40 mg hydroxypropylmethylcellulose 4000 mPas, 30 mg mannitol, and 10 mg magnesium stearate; and wherein at least 60% of the pralnacasan is released from the tablet not more than 30 minutes after administration, and at least 90% is released not more than 180 minutes after administration.

2. The extended release tablet as claimed in claim 1, wherein the two layers are disposed in layer form or as core and shell.

3. The extended release tablet as claimed in claim 2 disposed in core-shell form, with the extended release layer as the core.

* * * * *